United States Patent [19]
Wu et al.

[11] Patent Number: 6,092,243
[45] Date of Patent: Jul. 25, 2000

[54] SPORTS GOGGLES WITH CHANGEABLE LENSES AND IMPROVED WEARING COMFORT

[76] Inventors: Ching-Ying Wu, No. 25, Shin-Chi Village; Ming-Tien Fang, No. 52, Hai-Liau, Hai-Liau Village, both of An-Ding Shiang, Tainan Hsien, Taiwan

[21] Appl. No.: 09/198,257

[22] Filed: Nov. 24, 1998

[51] Int. Cl.[7] .................................................. A61F 9/02
[52] U.S. Cl. ........................... 2/441; 2/426; 2/440; 2/452
[58] Field of Search ............................... 2/426, 436, 437, 2/439, 441, 444, 452, 454, 440, 442, 443; 351/41, 178

[56] References Cited

U.S. PATENT DOCUMENTS

| | | | |
|---|---|---|---|
| 2,409,286 | 10/1946 | Joyce ............................................. | 2/14 |
| 3,440,662 | 4/1969 | O'Shea ......................................... | 2/14 |
| 3,505,680 | 4/1970 | Ring ............................................. | 2/14 |
| 4,989,274 | 2/1991 | Patelski ....................................... | 2/436 |
| 5,182,586 | 1/1993 | Bennato ....................................... | 351/47 |
| 5,511,251 | 4/1996 | Brakas ......................................... | 2/452 |
| 5,603,128 | 2/1997 | Chou ............................................ | 2/428 |
| 5,873,134 | 2/1999 | Chou ............................................ | 2/452 |

*Primary Examiner*—Gloria M. Hale
*Assistant Examiner*—Tejash Patel
*Attorney, Agent, or Firm*—Rosenberg, Klein & Lee

[57] ABSTRACT

A pair of sports goggles includes a strap made of plastic material. The strap includes two rings in a mediate portion thereof. A padding member of soft material is mounted to an inner side of each ring. Each padding member includes a receiving compartment for receiving a lens. Each padding member further includes at least one positioning pin projecting outward from a side thereof that faces the lens. Each lens includes at least one positioning hole through which a stem of the positioning pin on an associated padding member extends. An enlarged distal end of the positioning pin has a diameter slightly greater than that of the positioning hole of the associated lens.

1 Claim, 3 Drawing Sheets

SPORTS GOGGLES WITH CHANGEABLE LENSES AND IMPROVED WEARING COMFORT

BACKGROUND OF THE INVENTION

1. Field of the Invention

The present invention relates to a pair of sports goggles with changeable lenses and improved wearing comfort.

2. Description of the Related Art

FIG. 4 of the drawings illustrates a pair of typical sports goggles that includes a frame 40, a lens 41 mounted in the frame 40, a pair of temples 42, and a strap 43 connected between distal ends of the temples 42. In use, it is, however, found that the goggles will move up and down on the user's face and thus cause an uncomfortable feeling. The strap 43 may even be disengaged from the temples 42. In addition, the bridge portion and the templates 42 that bear against the skin of the user's face and ears also cause discomfort to the user. Furthermore, when the frame 40 or the lens 41 is broken, the user has to buy a new one even if the other elements are still usable. This also causes an increased cost for users, especially for those suffered from myopia or hypermetropia. The present invention is intended to provide an improved design for sports goggles to solve the above problems.

SUMMARY OF THE INVENTION

It is a primary object of the present invention to provide a pair of sports goggles that has improved wearing comfort.

It is another object of the present invention to provide a pair of sports goggles in which the lenses are changeable.

A pair of sports goggles in accordance with the present invention comprises a strap made of plastic material. The strap includes two rings in a mediate portion thereof, each ring defining a window and having an inner side. A padding member of soft material is mounted to the inner side of each ring. Each padding member includes a receiving compartment for receiving a lens. Each padding member further includes at least one positioning pin projecting outward from a side thereof that faces the lens. The positioning pin has a stem and an enlarged distal end. Each lens includes at least one positioning hole through which the stem of the positioning pin on an associated padding member extends. The enlarged distal end of the positioning pin has a diameter slightly greater than that of the positioning hole of the associated lens. This allows the user to disengage the padding member from the ring when replacement of the lens is required.

The positioning pin further includes a base that is formed on an end of the stem opposite to the enlarged distal end. The padding member is made of a number of layers, and the base of the positioning pin is securely held between two adjacent layers of the padding member.

Each lens may further include at least one ventilating hole or a holed button that communicates an interior of the padding member with the environment. This may relieve uncomfortable feeling to the eyes resulting from heat and prevent the lenses from being misted.

The strap further includes hooks and loops fasteners provided to two distal ends thereof for easy and releasable engagement between the two distal ends of the strap. This also allows the user to adjust the length of the strap to fit the user's head size.

Other objects, advantages, and novel features of the invention will become more apparent from the following detailed description when taken in conjunction with the accompanying drawings.

DETAILED DESCRIPTION OF THE PREFERRED EMBODIMENT

Figure 1:
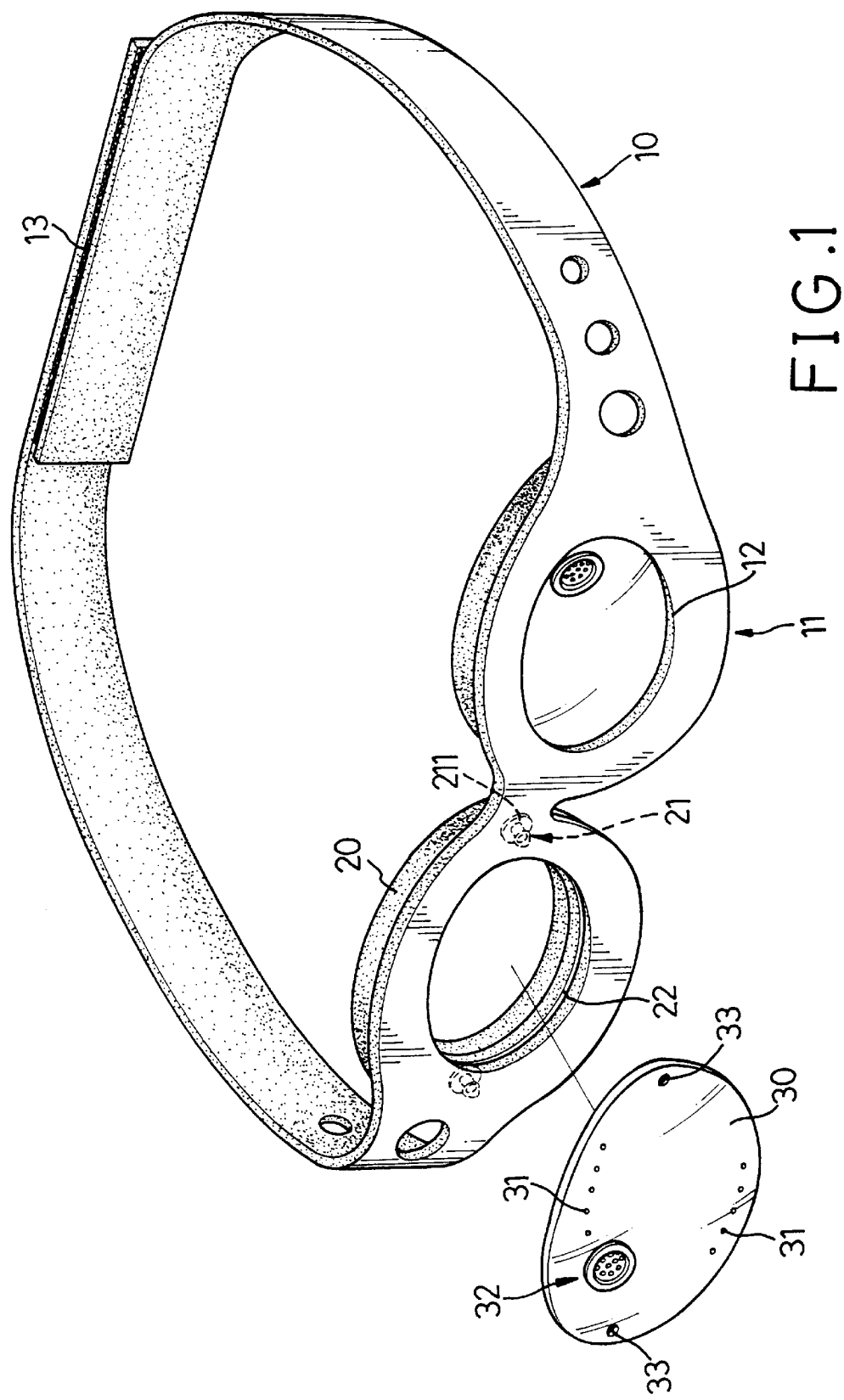
FIG. 1 is a perspective view, partly exploded, of a pair of sports goggles in accordance with the present invention.

Referring to FIG. 1, a pair of sports goggles in accordance with the present invention generally includes a strap 10 made of plastic material. The strap 10 includes two rings 11 in a mediate portion thereof, each ring 11 defining a window 12. The strap 10 further includes hooks and loops fasteners 13 provided to two distal ends thereof for easy and releasable engagement between the two distal ends of the strap 10. This also allows the user to adjust the length of the strap 10 to fit the user's head size.

Figure 2:
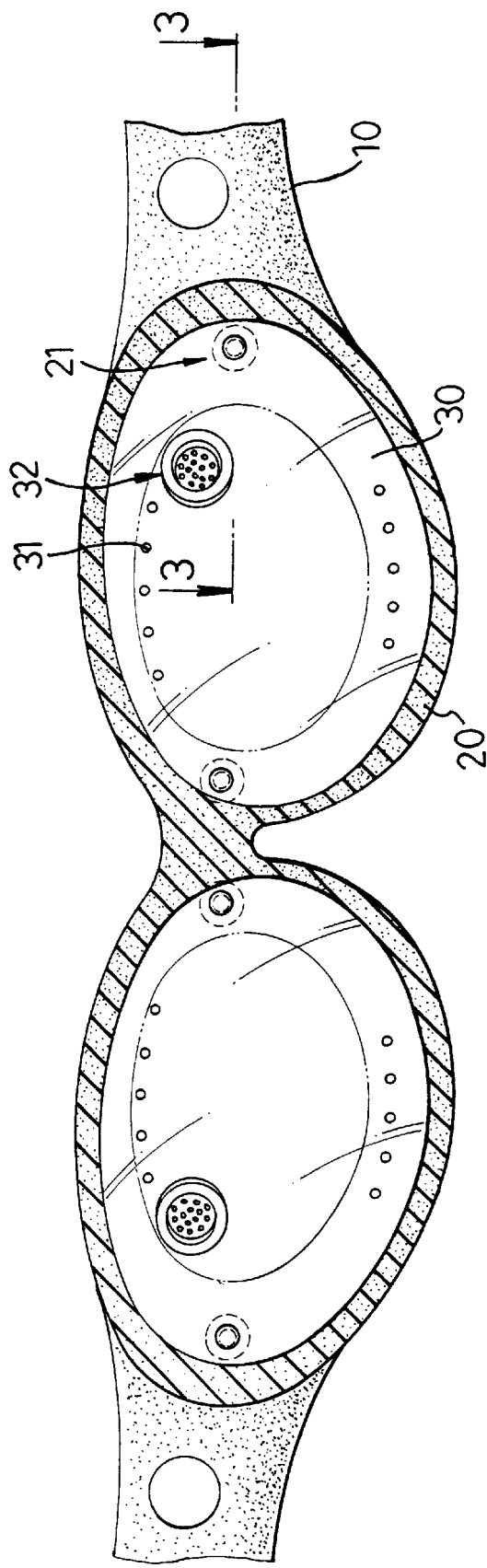
FIG. 2 is a front view of the frame and the lenses of the pair of sports goggles in Fig. 1.
Figure 3:
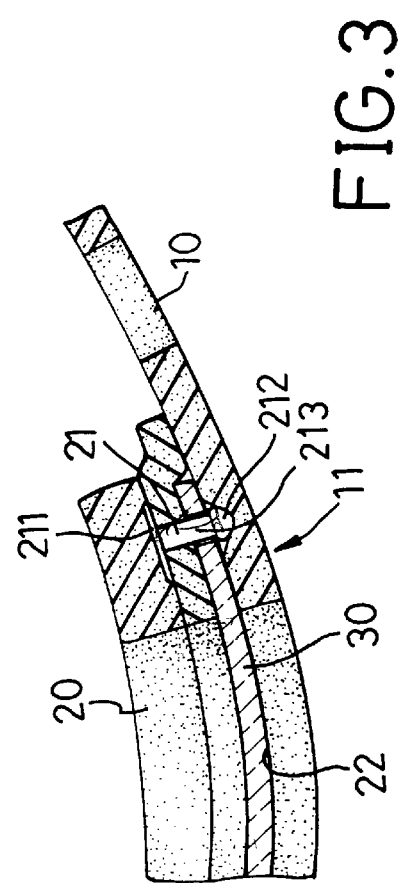
FIG. 3 is a sectional view taken along line 3—3 in FIG. 2.
Figure 4:
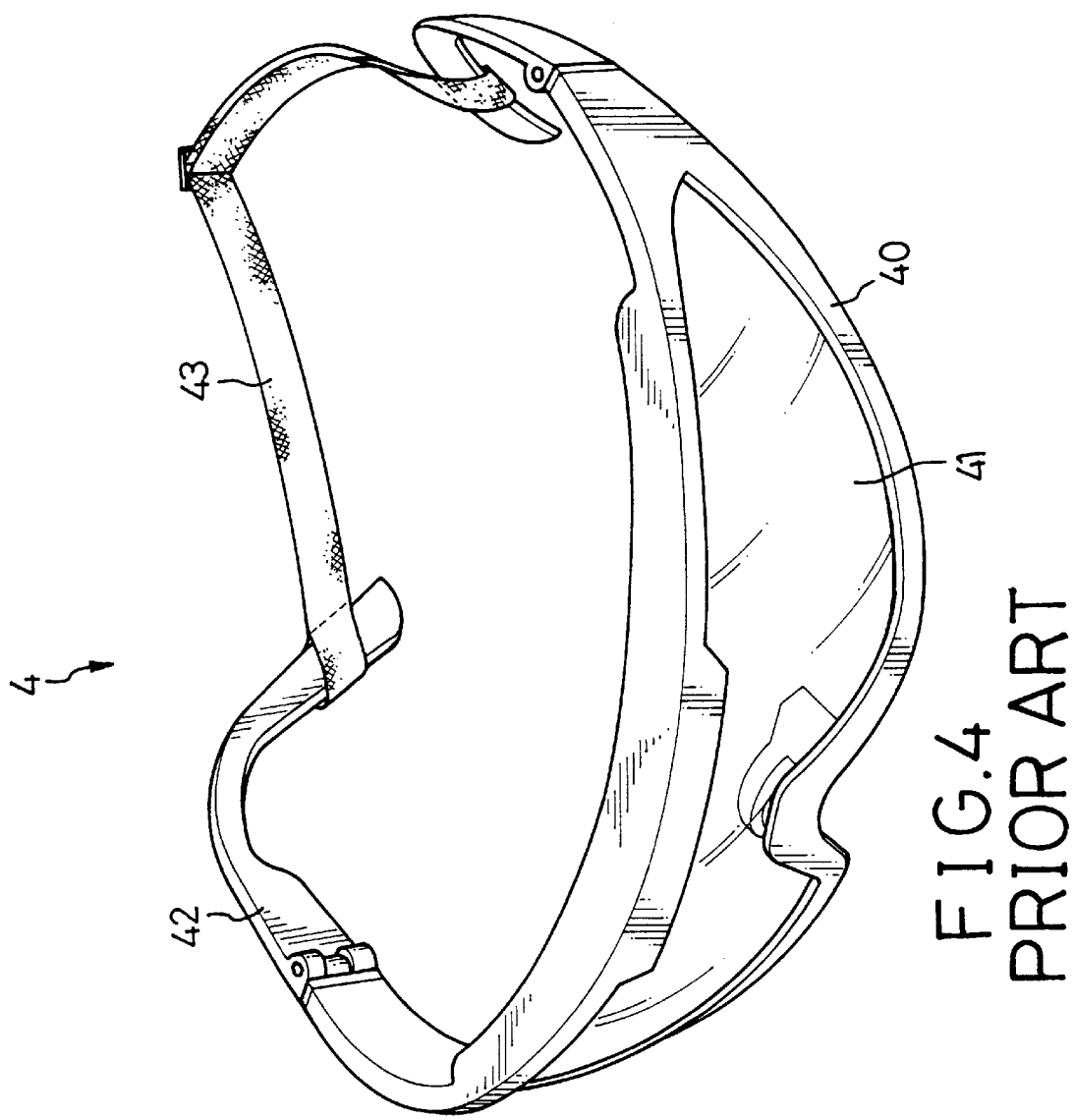
FIG. 4 is a perspective view of a pair of conventional sports goggles.

A padding member 20 of soft material is mounted to an inner side of each ring 11. As shown in FIGS. 2 and 3, each padding member 20 includes a receiving compartment 22 for receiving a lens 30. Each padding member 20 includes at least one positioning pin 21 projecting outward from a side thereof that faces the lens 30, the positioning pin 21 having a base 211, a stem 213, and an enlarged distal end 212. Each lens 30 includes at least one positioning hole 33 through which the stem 213 of an associated positioning pin 21 extends, best shown in FIG. 3. As shown in FIG. 3, the enlarged distal end 212 has a diameter slightly greater than that of the positioning hole 33 of the associated lens 30. This allows the user to remove the positioning pin 21 from the positioning hole 33 when changing the lens 30.

Each lens 30 may further include a number of ventilating holes 31 and/or a holed ventilating button 32 that communicates an interior of the padding member 20 with the environment. When in use, the padding members 20 provide a soft, comfortable contact with the user's eye-sockets, while the strap 10 provides a soft, comfortable contact with the temple areas and the ears of the user. In addition, hot air around the eye portions of the user as a result of sporting can exit via the ventilating holes 31 and/or the ventilating buttons 32. This may relieve uncomfortable feeling to the eyes resulting from heat and prevent the lenses 30 from being misted.

Referring to FIG. 3, the padding member 20 may include a number of layers corresponding to the length of the positioning pin 21. The base 211 of the positioning pin 21 may be securely held between two adjacent layers of the padding member 20.

According to the above description, it is appreciated that the sports goggles in accordance with the present invention provides improved wearing comfort, prevents from misting on the lenses, and allows replacement of lenses and heat exchange. In addition, replacement of lenses is convenient to users and economical when other elements are still usable, especially for those suffered from myopia or hypermetropia.

Although the invention has been explained in relation to its preferred embodiment, it is to be understood that many other possible modifications and variations can be made without departing from the spirit and scope of the invention as hereinafter claimed.

What is claimed is:

1. A pair of sports goggles, comprising:

a pair of lenses, each said lens having at least one positioning hole formed therethrough;

a strap made of a plastic material, said strap having two rings formed in a mediate portion thereof, each said ring defining a window and having an inner side; and, a pair of padding members, each of said pair of padding members being formed of a soft material and with a plurality of layers, each of said padding members being mounted to said inner side of a respective one of said rings and having a receiving compartment for receiving a respective one of said pair of lenses therein, each of said padding members including at least one positioning pin projecting from a side thereof for engagement with said at least one positioning hole of a respective one of said lenses, said at least one positioning pin having a base formed on one end thereof and secured between two adjacent layers of said plurality of layers of a respective padding member, said at least one positioning pin having a stem extending from said base and passing through said at least one positioning hole of a respective one of said lenses, said stem terminating in an enlarged distal end, said enlarged distal end having a diameter slightly greater than a diameter of said at least one positioning hole.

* * * * *

UNITED STATES PATENT AND TRADEMARK OFFICE
CERTIFICATE OF CORRECTION

PATENT NO.   : 6,092,243
DATED        : July 25, 2000
INVENTOR(S)  : Ying-Ching Wu It is certified that error appears in the above-identified patent and that said Letters Patent is hereby corrected as shown below:

Title page, item [76], inventors: Ching –Ying Wu should read –Ying-Ching Wu--

Signed and Sealed this

Twentieth Day of February, 2001

Attest:

NICHOLAS P. GODICI

Attesting Officer     Acting Director of the United States Patent and Trademark Office